(12) United States Patent
Aydeniz

(10) Patent No.: US 9,205,032 B2
(45) Date of Patent: Dec. 8, 2015

(54) PRESSED TABLET TISSUE APPLICATION BOX

(75) Inventor: Hailil Aydeniz, Istanbul (TR)

(73) Assignee: Ozsoy Organik Ternizlik Urunler Pazarlama Sanayi Ve Ticaret Limited Sirketi, Basaksehir Istanbul (TR)

( * ) Notice: Subject to any disclaimer, the term of this patent is extended or adjusted under 35 U.S.C. 154(b) by 109 days.

(21) Appl. No.: 13/812,476

(22) PCT Filed: May 6, 2011

(86) PCT No.: PCT/TR2011/000145
§ 371 (c)(1),
(2), (4) Date: Jul. 5, 2013

(87) PCT Pub. No.: WO2012/015370
PCT Pub. Date: Feb. 2, 2012

(65) Prior Publication Data
US 2013/0270149 A1    Oct. 17, 2013

(30) Foreign Application Priority Data

Jul. 26, 2010 (TR) .................................. 2010/06130

(51) Int. Cl.
*B65D 81/32* (2006.01)
*A47K 10/42* (2006.01)
(Continued)

(52) U.S. Cl.
CPC .......... *A61K 8/0208* (2013.01); *B65D 81/3222* (2013.01); *B65D 83/08* (2013.01); *A47K 10/16* (2013.01); *A47K 10/32* (2013.01); *A61M 35/006* (2013.01)

(58) Field of Classification Search
CPC ...... A61M 35/006; A61F 13/84; A61F 15/00; A45D 2200/058; A45D 40/0087; A45D 2040/0093; A47K 2010/3266; A47K 2010/3273; A47K 10/025; A47K 10/24; A47K 10/15; A47K 10/00; B65D 81/3266; B65D 81/32; B65D 83/08; B65D 35/242; B65D 75/5805; B65D 25/06; B65D 25/08; B65D 25/082; B65D 25/085; B65D 51/28; B65B 29/10; B65B 3/00; Y10S 215/08
USPC ................. 206/210, 494, 219, 568, 221, 222; 220/281, 4.21, 255, 255.1; 221/96; 215/DIG. 8; 426/112, 113; 604/2, 3; 222/212–215; 401/266, 261
See application file for complete search history.

(56) References Cited

U.S. PATENT DOCUMENTS 2,621,782 A * 12/1952 Reifers .......................... 206/540
2,789,725 A *  4/1957 Carper ........................... 401/125
(Continued)

FOREIGN PATENT DOCUMENTS

KR    10-2008-0000    *  1/2008  ............. A47K 10/16
KR    10-2009-0008    *  1/2009  ............. A47K 10/42

*Primary Examiner* — Mickey Yu
*Assistant Examiner* — Gideon Weinerth
(74) *Attorney, Agent, or Firm* — Kevin P. Crosby; GrayRobinson, P.A.

(57) ABSTRACT

A pressed sanitary tissue receptacle and dispenser comprised of a main body which defines nested inner and outer housing walls. The outer housing wall houses a quantity of liquid which is adapted to initially be isolated from a volume defined by the inner housing wall which houses the dry tissue. In one embodiment, the inner and outer housing walls are covered on their lower ends by a lower cover, and the upper ends of the inner and outer housing walls are covered on their upper ends by an upper cover. The upper cover may be a foil sheet. The liquid is permitted to enter the volume defined by the inner housing wall and become absorbed by the tissue upon the exertion of force on the upper cover, which causes the tissue to press against and deflect the lower cover in such a manner as to cause the lower cover to dislodge from sealing engagement with the inner cylinder.

10 Claims, 5 Drawing Sheets

(51) Int. Cl.
*A47K 10/32* (2006.01)
*A61K 8/02* (2006.01)
*B65D 83/08* (2006.01)
*A61F 13/40* (2006.01)
*A47K 10/16* (2006.01)

(56) References Cited

U.S. PATENT DOCUMENTS

| | | | |
|---|---|---|---|
| 3,145,838 A * | 8/1964 | Van Deusen | 206/221 |
| 3,466,131 A * | 9/1969 | Arcudi | 401/132 |
| 3,539,794 A * | 11/1970 | Kennerly et al. | 362/34 |
| 3,635,567 A * | 1/1972 | Richardson, Jr. | 401/132 |
| 3,696,919 A * | 10/1972 | Miles | 206/221 |
| 3,826,259 A * | 7/1974 | Bailey | 604/310 |
| 5,114,411 A * | 5/1992 | Haber et al. | 604/203 |
| 5,681,574 A * | 10/1997 | Haber et al. | 424/402 |
| 6,387,068 B1 * | 5/2002 | Naughton | 604/2 |
| 7,163,102 B2 * | 1/2007 | Palamara et al. | 206/219 |
| 7,681,725 B2 * | 3/2010 | Mueller et al. | 206/210 |
| 2005/0067423 A1 * | 3/2005 | Cho | 221/63 |
| 2007/0125667 A1 * | 6/2007 | Lee et al. | 206/219 |
| 2009/0232580 A1 * | 9/2009 | Castel et al. | 401/41 |
| 2009/0308776 A1 * | 12/2009 | Seo | 206/494 |
| 2010/0051576 A1 * | 3/2010 | Tran et al. | 215/386 |
| 2010/0202246 A1 * | 8/2010 | Huck et al. | 366/185 |
| 2013/0126549 A1 * | 5/2013 | Ader | 221/96 |
| 2014/0004227 A1 * | 1/2014 | Tran | 426/66 |

* cited by examiner

PRESSED TABLET TISSUE APPLICATION BOX

CROSS REFERENCE TO RELATED APPLICATIONS

This application claims priority under 35 U.S.C. Sections 119(a)-(d), 120, 363, and 365 to International Patent Application No. PCT/TR2011/000145, filed May 6, 2011 which designated the United States and at least one other country in addition to the United States and claimed priority to Turkish Application No. 2010/06130 filed Jul. 26, 2010. PCT/TR2011/000145 and Turkish Application No. 2010/06130 are expressly incorporated by reference herein in their entirety to form a part of the present disclosure.

BACKGROUND OF THE INVENTION

Field of the Invention

The present invention relates to a tissue storage container and dispenser. More specifically, the present invention relates to a personal compressed tablet tissue storage container and dispenser designed to be used in sectors such as hospitals, operating rooms, the entire health sector, tourism sector, service sectors, beauty culture services sector, etc.

The organic liquids to be used in the pressed tablet tissue storage container and dispenser box are selected from the group of materials comprising organic scent, water and pure water, disinfectant liquids and anti-bacteria liquids.

Preferably, organic scent liquid can be used based on the consumer's taste.

Usage of pure water is solely intended for the preservation of hygienic conditions.

Use of currently known models is does not solve the problem of preserving hygiene, and our model overcomes this problem.

As for disinfectant and anti-bacterial liquids, they suggest a practical and hygienic solution for health institutions.

Drawings that will serve a better understanding of the product have been provided and are described below.

DETAILED DESCRIPTION OF THE PREFERRED EMBODIMENT

Figure 1:
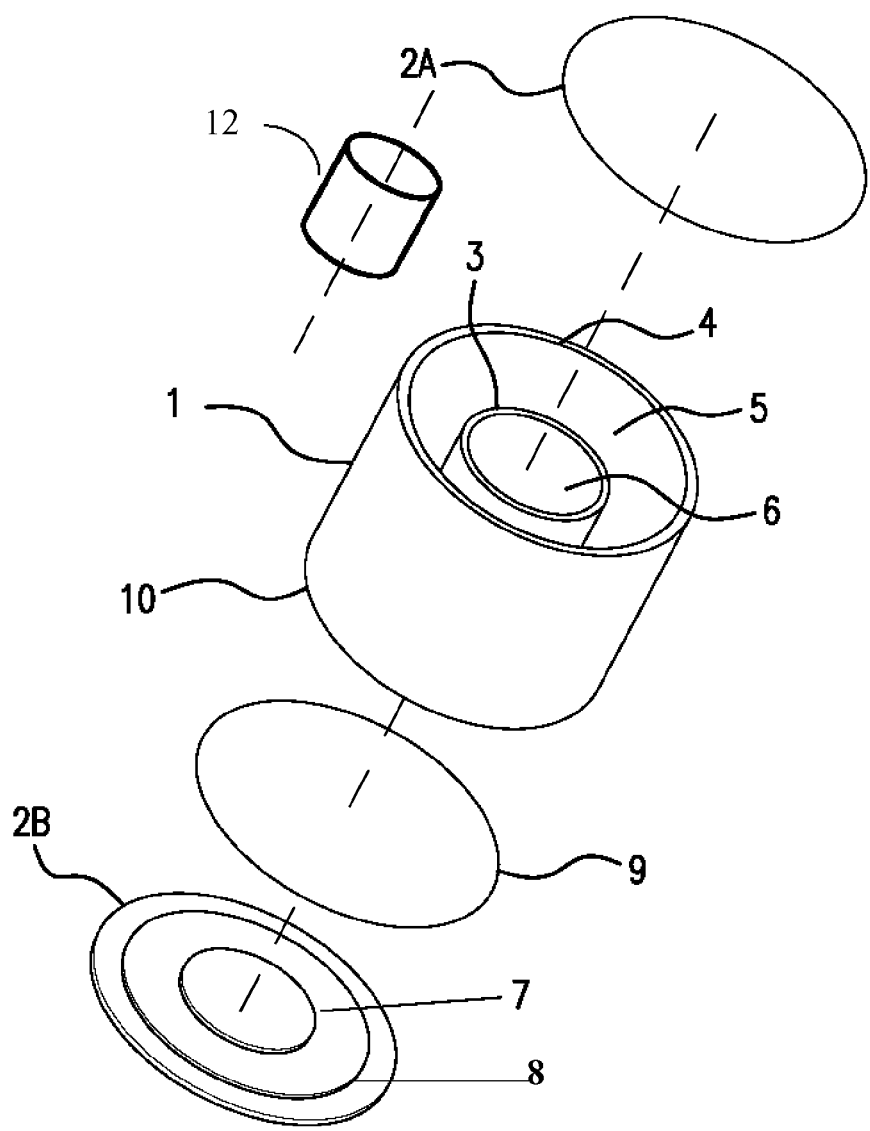
FIG. 1 is an exploded perspective view of an embodiment of the invention.

Names of the parts mentioned on the figures:
1. Main body
2A. Upper cover
2B. Lower cover
3. Inner cylinder
4. Outer cylinder
5. Liquid filling reservoir
6. Tablet tissue reservoir
7. Inner circular shoulder
8. Outer circular shoulder
9. Sealing sheet
10. Outer peripheral edge
11. Inner peripheral edge

DETAILED DESCRIPTION OF THE PREFERRED EMBODIMENT

The present invention is intended for personal use of individuals and relates to use in sectors such as hospitals, operating rooms, all the health sector, tourism sector, service sectors, beauty culture services sector, etc.

The liquids to be used in the pressed tablet tissue storage container and dispenser include organic scent, water and pure water, disinfectant liquids and anti-bacteria liquids.

A pressed sanitary tissue receptacle and dispenser is shown in FIG. 1. The preferred embodiment of the storage container and dispenser comprises a main body 1, an upper cover 2A, a lower cover 2B, an inner cylinder 3, an outer cylinder 4, a liquid filling reservoir 5, a tablet tissue reservoir 6, an inner circular shoulder 7, and an outer circular shoulder 8. Other embodiments may include a sealing sheet 9 engaged with the outer peripheral edge 10 of the main body 1 and the lower cover 2B.

The apparatus consists of two main parts. The main body 1 has two nested cylinders. Inner cylinder 3 is open on the sides facing the upper cover 2A and lower cover 2B and the outer cylinder 4 has a liquid reservoir 5 for various liquids that is open on the sides facing the upper cover 2A and lower cover 2B. Outer cylinder 4 may be open on the side facing upper cover 2A to allow for filling although the preferred usage will have outer cylinder 4 and liquid reservoir 5 filled with liquid through the side facing lower cover 2B. The inner cylinder 3 houses tissue 12 in the tablet tissue reservoir 6.

Figure 2:
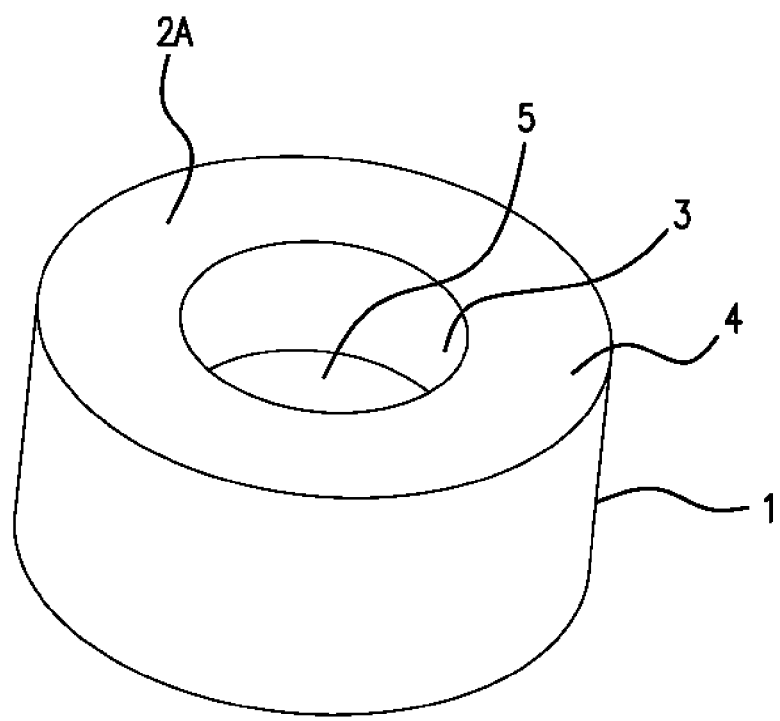
FIG. 2 is a perspective view of the upper part of the main body.

FIG. 2 shows the main body 1. The upper cover 2A is preferably a foil sheet that can be pierced by any object, including a human finger. FIG. 2 shows the main body 1 after it has been pierced.

Figure 3:
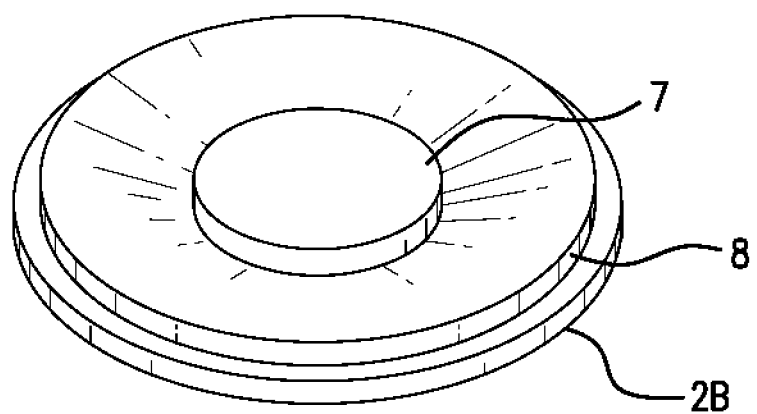
FIG. 3 is a perspective view of the lower cover.

FIG. 3 provides a detailed view of lower cover 2B. Lower cover 2B features an outer circular shoulder 8 and an inner circular shoulder 7 which make sure the main body 1 and the lower cover 2B are connected and the two pieces joined together in a way they would not detach such as by engaging the outer circular shoulder 8 with the outer peripheral edge 10 of the main body 1, as can be seen in FIG. 1.

Figure 4:
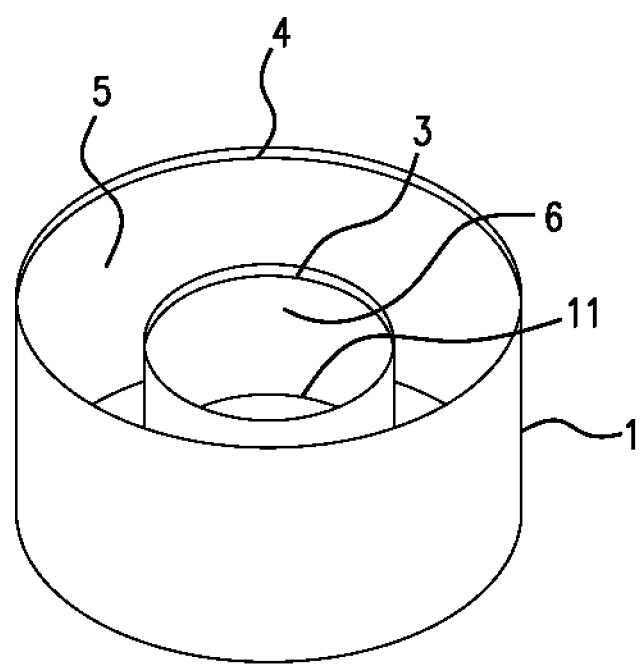
FIG. 4 is a bottom perspective view of the upper part of the main body.

FIG. 4 shows the main body 1 without the upper cover 2A. A perspective of the inner peripheral edge 11 of the inner cylinder 3 can be seen in this figure. This inner peripheral edge 11 is what engages the inner circular shoulder 7 of the lower cover 2B. The inner circular shoulder 7 is what ensures that the liquid filling reservoir 5 is insulated from the tablet tissue. This is due to the concave posture of the lower 2B when in a resting position.

Another option is to include a sealing sheet 9, as shown in FIG. 1, that provides further insulation between the liquid reservoir 5 and the tablet tissue reservoir 6. For example, a foil sheet can be put in between the lower cover 2B and the table tissue reservoir 6.

Figure 5A:
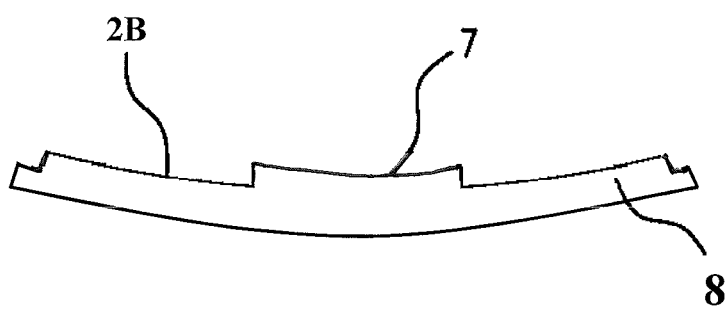
FIG. 5A is a side elevational view of the lower cover in a convex orientation.
Figure 5B:
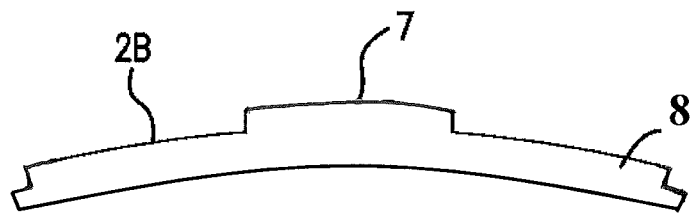
FIG. 5B is a side elevational view of the lower cover in a concave orientation.

Preferably, as shown in FIG. 5B, the lower cover 2B is first in a convex position. After the tablet tissue 12 is pressed into the tablet tissue reservoir 6 due to downward pressure caused by finger impact, the tissue 12 will then preferably absorb whatever liquid is located in the liquid reservoir 5. Pressure on the tissue 12 causes the inner circular shoulder 7 of the lower cover 2B to deform from the concave orientation shown in FIG. 5A to the convex orientation shown in FIG. 5B, dislodging inner circular shoulder 7 from the lower peripheral edge 10 of the inner cylinder 3, thereby permitting the liquid to enter tablet tissue reservoir 6 and be absorbed by the tissue 12.

Preferably, the lower cover 2B is made of a material with high plastic strain characteristics so as to facilitate the transition between concave and convex.

The invention offers employability in hospitals, operating rooms, all the health sector, tourism sector, service sectors, beauty culture services and similar sectors.

The invention, in its preferred embodiment, is directed to a pressed sanitary tissue receptacle and dispenser comprised of a main body 1 which includes nested inner and outer cylinders 3 and 4, respectively. The outer cylinder 4 defines a liquid reservoir 5 which houses a quantity of liquid which is adapted to initially be isolated from the inner or tablet tissue reservoir 6 and the dry tissue sealingly housed therein. In one embodiment, the inner and outer cylinders are covered on their lower ends by a lower cover 2B, and the upper ends of the inner cylinder 3 and outer cylinder 4 are covered on their upper ends by an upper cover 2A. The upper cover 2A may be a pierceable foil sheet. The lower cover 2B may be a flexible disc having an outer circular shoulder 8 which nests with an outer peripheral edge 10 of the outer cylinder 4, and an inner circular shoulder 7 which nests with a lower peripheral edge 11 of the inner cylinder 3. The liquid is permitted to enter the tablet tissue reservoir 6 and become absorbed by the tissue 12 upon exertion of force on the upper cover 2A, which causes the tissue 12 to press against and deflect the lower cover 2B in such a manner as to cause the inner circular shoulder 7 to disengage from the lower peripheral edge 11 of the inner cylinder 3. Representative concave and convex orientations of lower cover 2B are shown in FIGS. 5A and 5B.

Benefits, other advantages, and solutions to problems have been described above with regard to specific embodiments of the present invention. However, the benefits, advantages, solutions to problems, and any element(s) that may cause or result in such benefits, advantages, or solutions to become more pronounced are not to be construed as a critical, required, or essential feature or element of any or all the claims. The invention is defined solely by the appended claims including any amendments made during the pendency of this application and all equivalents of those claims as issued.

Now that the invention has been described,

What is claimed is:

1. A sanitary tissue receptacle and dispenser comprised of:
a main body defined by inner and outer housing walls, a liquid reservoir volume between the inner and outer housing walls defining a liquid reservoir, a tissue storage volume within the inner housing wall defining a tissue storage reservoir;
a lower cover adapted to cover open lower ends of the inner and outer housing walls;
a pierceable upper cover adapted to cover open upper ends of the inner and outer housing walls;
the lower cover defining an inner shoulder adapted to sealingly but disengagingly nest within the open lower end of the inner housing wall and an outer shoulder adapted to sealingly nest with the open lower end of the outer housing wall, the lower cover being sealingly connected to the open lower end of the outer housing wall;
a quantity of liquid housed within the liquid reservoir; and
a tissue housed within the tissue storage reservoir.

2. The sanitary tissue receptacle and dispenser of claim 1, wherein the upper cover is a pierceable foil sheet sealingly connected to upper peripheral edges of the inner and outer housing walls, and the lower cover is a flexible disc.

3. The sanitary tissue receptacle and dispenser of claim 1, wherein: the liquid is permitted to enter the tissue storage reservoir and become absorbed by the tissue upon the exertion of force on the upper cover, which causes the tissue to press against and deflect the lower cover in such a manner as to cause the inner shoulder to dislodge from the inner housing wall while the outer shoulder remains in substantially the same position.

4. The sanitary tissue receptacle and dispenser of claim 1, wherein:
the lower cover has a convex shape when the inner shoulder is nested with the inner housing wall, and takes either a concave or flat shape when the tissue is pressed against and deflects the lower cover such that the quantity of liquid in the liquid reservoir interacts with the tissue.

5. The sanitary tissue receptacle and dispenser of claim 1, further comprising a sealing sheet placed between the lower cover and the tissue storage reservoir.

6. A sanitary tissue receptacle and dispenser comprised of:
a main body which includes nested inner and outer housing walls, a liquid reservoir being defined by a volume between the inner and outer housing walls, a tissue storage reservoir being defined by the inner housing wall, the liquid reservoir housing a quantity of liquid which is isolated from the tissue storage reservoir, a lower cover defining an inner shoulder adapted to sealingly but disengagingly nest with the inner housing wall and an outer shoulder that remains substantially in the same position while in use adapted to sealingly nest with the outer housing wall, the lower cover being sealingly connected to the outer housing wall of the main body, and an upper cover.

7. The sanitary tissue receptacle and dispenser of claim 6, further comprising:
an upper cover adapted to cover open upper ends of the inner and outer housing walls; and
the lower cover further adapted to cover open lower ends of the inner and outer housing walls.

8. The sanitary tissue receptacle and dispenser of claim 6, wherein:
the upper cover is a pierceable foil sheet sealingly connected to upper peripheral edges of the inner and outer housing walls; and
the lower cover is a flexible disc defining an outer shoulder which nests with a lower peripheral edge of the outer housing wall, and an inner shoulder which nests with a lower peripheral edge of the inner housing wall.

9. The sanitary tissue receptacle and dispenser of claim 6, wherein:
the liquid is permitted to enter the tissue storage reservoir and become absorbed by the tissue upon the exertion of force on and piercing of the upper cover, which causes the tissue to press against and deflect the lower cover in such a manner as to cause the inner shoulder to dislodge from the inner housing wall.

10. The sanitary tissue receptacle and dispenser of claim 7, further comprising a foil sheet placed between the lower cover and the tissue storage reservoir.

* * * * *